(12) United States Patent
Kim et al.

(10) Patent No.: US 9,777,046 B2
(45) Date of Patent: Oct. 3, 2017

(54) REPEBODY AGAINST IMMUNOGLOBULIN G AND USES THEREOF

(71) Applicant: Korea Advanced Institute of Science and Technology, Daejeon (KR)

(72) Inventors: Hak-Sung Kim, Daejeon (KR); Woosung Heu, Daejeon (KR); Joong-Jae Lee, Daejeon (KR); Seong-Min Jo, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 451 days.

(21) Appl. No.: 14/322,864

(22) Filed: Jul. 2, 2014

(65) Prior Publication Data
US 2015/0018533 A1 Jan. 15, 2015

(30) Foreign Application Priority Data
Jul. 10, 2013 (KR) .......................... 10-2013-0081009

(51) Int. Cl.
*C07K 14/195* (2006.01)
*C07K 14/705* (2006.01)
*C07K 16/06* (2006.01)

(52) U.S. Cl.
CPC .......... *C07K 14/195* (2013.01); *C07K 14/705* (2013.01); *C07K 16/065* (2013.01); *C07K 2319/70* (2013.01)

(58) Field of Classification Search
None
See application file for complete search history.

(56) References Cited

FOREIGN PATENT DOCUMENTS

| | | | | |
|---|---|---|---|---|
| DE | WO 2011048043 A1 * | 4/2011 | ......... | C07K 16/4283 |
| KR | 10-2013-0098089 A | 9/2013 | | |

OTHER PUBLICATIONS

Burgess et al. J Cell Biol. Nov. 1990;111(5 Pt 1):2129-38.*
Lazar et al., Mol Cell Biol. Mar. 1988;8(3):1247-52.*
Rudikoff et al., Proc Natl Acad Sci U S A. Mar. 1982;79(6):1979-83.*
Lee et al., Proc Natl Acad Sci U S A. Feb. 28, 2012;109(9):3299-304. doi: 10.1073/pnas.1113193109. Epub Feb. 10, 2012.*
Binz, H., et al, "Engineering novel binding proteins from nonimmunoglobulin domains", "Nature Biotechnology", Oct. 6, 2005, pp. 1257-1268, vol. 23, No. 10.
Lee, S., et al., "Design of a binding scaffold based on variable lymphocyte receptors of jawless vertebrates by module engineering", "PNAS", Feb. 28, 2012, pp. 3299-3304, vol. 109, No. 9.

* cited by examiner

*Primary Examiner* — Michael Szperka
(74) *Attorney, Agent, or Firm* — Hultquist, PLLC; Steven J. Hultquist

(57) ABSTRACT

The present invention relates to a polypeptide (repebody) selectively bound to an immunoglobulin G, a polynucleotide which encodes the repebody, a vector containing the polynucleotide, a recombinant microorganism in which the polynucleotide is introduced, a method for producing the repebody using the recombinant microorganism, and a method for immobilizing or purifying an immunoglobulin G using the repebody. The repebody according to the present invention is useful as utilized for immobilization of an immunoglobulin G, purification of an immunoglobulin G, and production of an immunosensor, since the repebody selectively bound to an immunoglobulin G.

6 Claims, 6 Drawing Sheets

REPEBODY AGAINST IMMUNOGLOBULIN G AND USES THEREOF

CROSS-REFERENCE TO RELATED APPLICATION

This application claims priority under 35 U.S.C. §119 of Korean Patent Application No. 10-2013-0081009 filed on Jul. 10, 2013. The disclosure of such Korean patent application is hereby incorporated herein by reference in its entirety, for all purposes.

TECHNICAL FIELD

The present invention relates to a polypeptide (repebody) against immunoglobulin G (IgG) and a use thereof, and more specifically, to a repebody selectively bound to IgG, a polynucleotide which encodes the repebody, a vector containing the polynucleotide, a recombinant microorganism in which the polynucleotide is introduced, and a method for producing the repebody using the recombinant microorganism.

BACKGROUND ART

Immunoglobulin, which is a glycoprotein performing an antibody function neutralizing external antigens such as viruses, bacteria, and the like, is present in the blood or the tissue fluid. Among them, immunoglobulin G has the maximum content. The immunoglobulin G present in the blood or the tissue fluid is an important material protecting body from other external materials to be currently and widely used in fields such as protein therapeutics, diagnosis, and the like.

As the immunoglobulin G becomes increasingly used, an importance of a purification technology thereof is also increased. The currently used technology for purification of the immunoglobulin G is an affinity chromatography using protein A found in *Staphylococcus*. The protein A has a property of binding to Fc fragment of immunoglobulin, and thereby being used in purification of the immunoglobulin G. However, the purification method using the protein A has a disadvantage in view of high cost. In addition, elution in an antibody purification process is conducted under significantly strong acidic conditions of about pH 2 to 3, such that a probability of seriously damaging an antibody is extremely high. Further, since the protein A is significantly unstable in a high-pH solution used in the production process, the times of reuse of the protein A column is decreased, and thus, the production cost of the antibody is increased.

Accordingly, the present inventors studied to develop a repebody having a general binding protein frame with a binding capacity to various proteins, and as a result thereof, selected a novel protein having a binding capacity against immunoglobulin G, by modularity which is a structural characteristic of the repebody and the total structure analysis, based on a random mutant library. In addition, they produced and selected a novel polypeptide which is a novel repebody selectively bound to the immunoglobulin G through beneficial mutation obtained by predicting protein complex structure as a basis, and confirmed that the repebody is selectively bound to the immunoglobulin G, thereby completing the present invention.

DISCLOSURE OF INVENTION

Technical Problem

An object of the present invention is to provide a repebody selectively bound to IgG, a polynucleotide which encodes the repebody, a vector containing the polynucleotide, a recombinant microorganism in which the polynucleotide is introduced, and a method for producing the repebody using the recombinant microorganism.

Another object of the present invention is to provide a method for immobilizing or purifying IgG using the repebody.

Technical Solution

In order to achieve the foregoing objects, the present invention provides a repebody selectively bound to an immunoglobulin G in which an N-terminal of Leucine rich repeat (LRR) family protein having an alpha-helix capping motif; a modified repeat module of variable lymphocyte receptor (VLR) protein and a C-terminal of the VLR protein are fused, wherein said modified repeat module of the VLR protein, and said C-terminal of the VLR protein are represented by the amino acid sequence of SEQ ID NO: 6.

In addition, the present invention provides a repebody selectively bound to an immunoglobulin G in which an N-terminal of Leucine rich repeat (LRR) family protein having an alpha-helix capping motif; a modified repeat module of variable lymphocyte receptor (VLR) protein and a C-terminal of the VLR protein are fused, wherein amino acid(s) at one or two or more position(s) selected from a group consisting of Nos: 78, 80, 82, and 83 in the amino acid sequence of SEQ ID NO: 6 is mutated.

The present invention provides a polynucleotide which encodes the repebody as described above.

The present invention provides a vector which contains the polynucleotide as described above.

The present invention provides a recombinant microorganism in which the polynucleotide as described above or the vector as described above is introduced.

The present invention provides a method for producing a repebody selectively bound to an immunoglobulin G, wherein the method comprises: (i) Expressing the repebody by culturing the recombinant microorganism as described above; and (ii) Recovering the expressed repebody.

The present invention provides a method for purifying an immunoglobulin G antibody, wherein the method comprises: (i) Treating a column onto which the repebody as described above is adsorbed with a composition comprising an antibody; and (ii) Eluting the antibody attached to the column of the step (i).

The present invention provides a method for immobilizing an immunoglobulin G, wherein the method comprises: (i) Surface-treating a solid substrate by attaching the repebody as described above onto the solid substrate; and (ii) Binding an immunoglobulin G to the surface-treated solid substrate.

The present invention provides immunosensor in which an immunoglobulin G is immobilized onto a solid substrate surface-treated with the repebody as described above, using the repebody as a mediator.

BEST MODE FOR CARRYING OUT THE INVENTION

Figure 1:
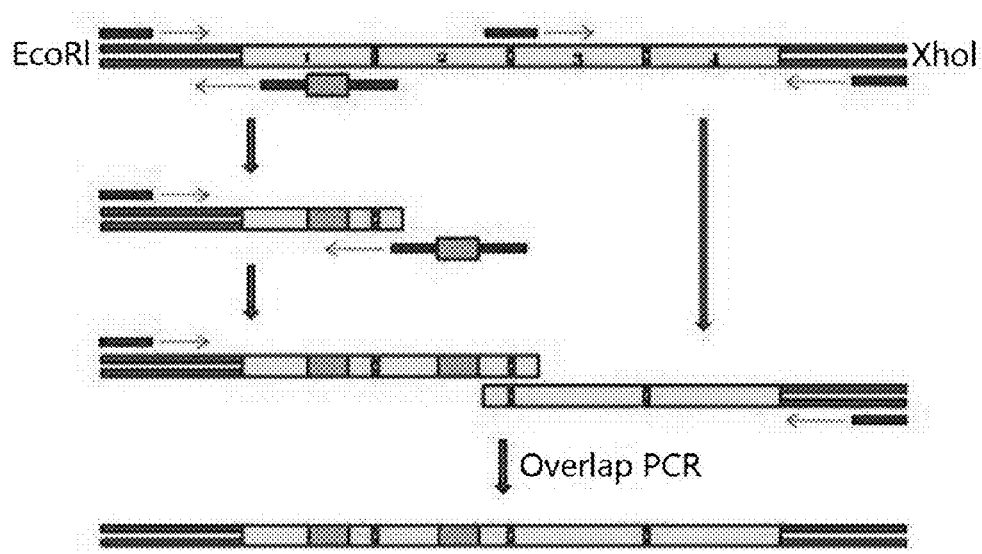
FIG. 1 is an entire schematic diagram of the overlap polymerase chain reaction (PCR) performed based on a module; Each yellow part indicates a Variable repeat module and a total of four Variable repeat modules are positioned on a polypeptide; A red linear rod indicates a primer used in experiments and a green part of the printer indicates sequence of a concave region containing NNK synonymous codon.

Unless defined otherwise, all the technical and scientific terms used herein have the same meanings as those generally understood by persons skilled in the art to which the present invention pertains. Generally, the nomenclature used herein are well known and commonly employed in the art.

The present inventors constructed a library randomly including a repeat module of a polypeptide in which an N-terminal of Leucine rich repeat (LRR) family protein having an alpha-helix capping motif, a modified repeat module of variable lymphocyte receptor (VLR) protein, and a C-terminal of the VLR protein are fused, in order to develop a novel polypeptide (repebody) capable of being selectively bound to immunoglobulin G (IgG), and effectively immobilizing or purifying IgG. The polypeptide included in the library may be encoded by a polynucleotide sequence of SEQ ID NO: 1 or a polynucleotide sequence having homology of 75%, preferably 85%, more preferably 90%, further preferably 95% or more, with the polynucleotide sequence of SEQ ID NO: 1. In addition, the library may be formed of phagemid including the polynucleotide. In the present invention, the term "phagemid" means a circular polynucleotide molecule derived from a phage which is a virus having *E. coli* as a host and includes sequences of proteins and surface-proteins required for propagation and proliferation. A recombinant phagemid may be produced using gene recombinant technology well known in the art, and site-specific DNA cleavage and connection may be performed by an enzyme, generally known in the art, and the like. The phagemid may include a signal sequence or leader sequence for secretion in addition to expression regulating factors such as a promoter, an operator, an initiation codon, a termination codon, an enhancer and may be mainly used in a method for labeling the protein on a surface of the phage by fusing a desired protein with a surface protein of the phage. The promoter of the phagemid is mostly inducible and may include a selective marker for selecting a host cell. For an object of the present invention, the phagemid may be a polynucleotide of SEQ ID NO: 2, including MalEss, DsbAss or PelBss which is a signal sequence or a leader sequence for expressing and secreting the polynucleotide which encodes the polypeptide constructing the library, and including a histidine-tag for confirming expression of a recombinant protein on a surface of the phage, and a polynucleotide which encodes gp3 domain which is a kind of a surface protein of M13 phage for expression on the surface of the phage, but the present invention is not particularly limited thereto.

The present inventors firstly selected a novel polypeptide (SEQ ID NO: 3, Repebody-E10) which is a repebody having excellent binding capacity to IgG, using a phage display method using the library including the phagemid.

Therefore, in one aspect, the present invention is directed to a repebody selectively bound to an immunoglobulin G in which an N-terminal of Leucine rich repeat (LRR) family protein having an alpha-helix capping motif; a modified repeat module of variable lymphocyte receptor (VLR) protein and a C-terminal of the VLR protein are fused, wherein said modified repeat module of the VLR protein, and said C-terminal of the VLR protein are represented by the amino acid sequence of SEQ ID NO: 6. Here, SEQ ID NO: 6 corresponds to the part of position Nos: 84 to 266 of the amino acid of SEQ ID NO: 3.

The present inventors mutated the selected polypeptide in order to obtain a polypeptide having more improved binding capacity to IgG than that of the firstly selected polypeptide. To this end, a repebody having excellent binding capacity was secured by rational design scheme based on a complex structure of the selected polypeptide of SEQ ID NO: 3 and IgG. In detail, among the selected polypeptide amino acid sequence of SEQ ID NO: 3, an amino acid at a position which is expected to improve the binding capacity to IgG was mutated to obtain a novel polypeptide specifically bound to IgG (SEQ ID NO: 4 Repebody D10 and SEQ ID NO: 5 Repebody F4). That is, a complex of the polypeptide of SEQ ID NO: 3 and IgG was expressed in *E. coli* and the amino acid of the repebody adjacent to IgG was partially mutated, thereby selecting a polypeptide having an increased to IgG. In an exemplary embodiment of the present invention, polypeptides of which (an) amino acid(s) at one or two or more position(s) selected from a group consisting of Nos: 161, 163, 165 and 166 in polypeptide amino acid sequence represented by Repebody-E10 (SEQ ID NO: 3) (which is the same as Nos: 78, 80, 82, and 83 in polypeptide amino acid sequence represented by SEQ ID NO: 6) is mutated were produced and among them, polypeptides of SEQ ID NOs: 4 and 5 having excellent biding capacity to IgG were selected. The novel polypeptide (SEQ ID NOs: 4 and 5) produced by mutation of the amino acid of SEQ ID NO: 3 at a specific position is selectively bound to IgG is useful for immobilization, purification, and the like, of IgG.

Therefore, in another aspect, the present invention is directed to a repebody selectively bound to an immunoglobulin G in which an N-terminal of Leucine rich repeat (LRR) family protein having an alpha-helix capping motif; a modified repeat module of variable lymphocyte receptor (VLR) protein and a C-terminal of the VLR protein are fused, wherein amino acid(s) at one or two or more position(s) selected from a group consisting of Nos: 78, 80, 82, and 83 in the amino acid sequence of SEQ ID NO: 6 is mutated.

Here, in the present invention, the N-terminal of Leucine rich repeat (LRR) family protein having an alpha-helix capping motif is preferably an N-terminal of an internalin protein. In the present invention, the term "internalin protein" is a kind of the LRR family protein expressed in a *Listeria* strain, and it is known that the internalin protein has an N-terminal structure different from that of the LRR family proteins in which a hydrophobic core are uniformly distributed through the entire molecule to thereby be stably expressed in microorganisms. It is considered that since the N-terminal of the internalin protein which is the most important in folding a repeat module is derived from a microorganism and has a stable shape including an alpha-helix, such that the internalin protein is stably expressed in microorganisms. The internalin protein used in fusion of the present invention may limitlessly include any internalin protein which is expected to have an N-terminal structure similar thereto and play an important role in protein folding, and as an example thereof, internalin protein A, B, C, H, J, or the like, preferably, internalin protein B, may be used. However, since the internalin proteins A to J are significantly similar to the internalin protein B in view of a structure, and the root mean square deviation (RMSD) values thereof with the N-terminal (36 to 11) of the internalin protein B through a structure alignment are 0.6 [internalin protein A (36 to 115)], 0.793 [internalin protein C (36 to 115)], 0.619 [internalin protein H (36 to 115)], and 0.862 [(internalin protein J (57 to 131)), respectively, which are significantly similar to that of internalin protein B, the internalin proteins A to J may be used instead of the internalin protein B.

In the present invention, the term "N-terminal of an (or the) internalin protein" of the present invention means an N-terminal of the internalin protein required for soluble expression and folding of the protein, and means a repeat module of the alpha-helix capping motif and the internalin protein. The N-terminal of the internalin protein may limitlessly include any N-terminal of the internalin protein required for soluble expression and folding of the protein, and as an example thereof, an alpha-helix capping motif "ETITVSTPIKQIFPDDAFAETIKANLKKKSVT-DAVTQNE (SEQ ID NO: 9)" and the repeat module may be included. The repeat module pattern may be "LxxLxxLx-LxxN". In the repeat module, L means alanine, glycine, phenylalanine, tyrosine, leucine, isoleucine, valine, or tryptophan; N means asparagine, glutamine, serine, cysteine or threonine and x means any amino acid. In addition, the N-terminal of the internalin protein of the present invention may be the N-terminal of the internalin B protein which is SEQ ID NO: 10; however, may be limitlessly used as long as the N-terminal has high structural similarity depending on a kind of the LRR family protein, and the most stable amino acid may be selected by calculation of a binding energy, and the like, and the amino acid of the module corresponding thereto may be mutated. The N-terminal of the internalin protein selected by the method according to the present invention may consist of any one amino acid sequence selected from SEQ ID NOs: 11 to 13. SEQ ID NOs: 11 to 13 correspond to position Nos: 1 to 83 of the amino acid of SEQ ID NOs: 3 to 5.

In the present invention, the term "immunoglobulin G (IgG)" is one kind of globulin protein having an antibody activity contained in body fluids such as blood serum, and the like, and is occupied by about 70% of the immunoglobulin. IgG is a glycoprotein where a molecular weight thereof is about 160,000, a molecular model is Y type, two upper ends are bound to an antigen, and a lower end (Fc part) is allowed to bind the antibody which binds to the antigen to a cell or a complement thereby having a biological activity. IgG participates in overall immune reaction to generate neutralization of toxins or viruses, sedimentation and flocculation reaction.

Figure 4:
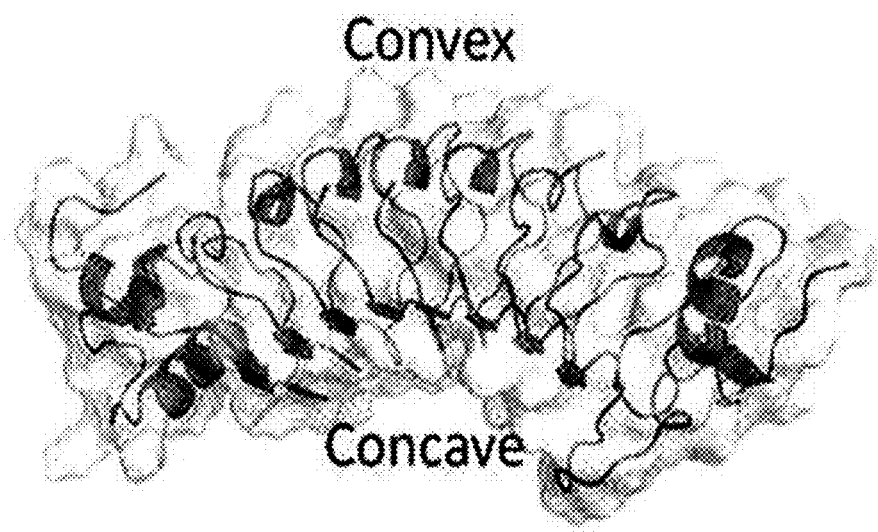
FIG. 4 is a schematic diagram showing an entire protein structure of repebody, divided into a concave region recognizing biomolecule and a convex region which is important in maintaining the structure.

In the present invention, the term "repebody" is a polypeptide optimized by consensus design through fusion of the N-terminal of the internalin B having the LRR protein structure and the VLR based on the structural similarity. The repebody protein may be structurally divided into a concave region and a convex region (FIG. 4). Here, it is known that the concave region has high variety of the sequence and is important in protein interaction. On the contrary, the convex region serves to stably maintain the entire structure of protein based on the highly conserved sequence. The repebody protein may include all fusion LRR family protein obtained by using all proteins included in the LRR family having the repeat module to improve the solubility expression and biophysical properties of protein of all protein by the above-described method.

In the present invention, the term "variable lymphocyte receptor (VLR)" is a kind of the LRR family protein expressed in a hagfish and a lamprey, performing an immune function, and has been in the spotlight as a frame capable of binding to various antigen materials. Since the polypeptide in which the N-terminal of the internalin B protein and the VLR protein are fused has an increased solubility and an increased expression amount as compared to the VLR protein in which the internalin B protein is not fused, the polypeptide may be useful for production a novel protein therapeutic agent based on the polypeptide. The improvement of the expression amount as described above suggests that the polypeptide of the present invention has largely improved economic feasibility, and the increase in the expression amount of the fused polypeptide in which the internalin B protein and the VLR protein are fused was firstly developed by the present inventors (Korean Patent Application No. 10-2012-0019927).

In the present invention, the term "Leucine rich repeat (LRR) family protein" means a protein formed by combination of modules in which leucine is repeated at a certain position, (i) it has one or more LRR repeat modules, (ii) the LRR repeat module consists of 20 to 30 amino acids, (iii) the LRR repeat module has "LxxLxxLxLxxN" as a conservation pattern, wherein L means hydrophobic aminoacids such as alanine, glycine, phenylalanine, tyrosine, leucine, isoleucine, valine, and tryptophan; N means asparagine, glutamine, serine, cysteine or threonine and x means any amino acid, and (iv) the LRR family protein means a protein having a three dimensional structure like horseshoe. The LRR family protein of the present invention may include all mutants having the sequence which is already known or found by newly induced mRNA or cDNA, as well as the sequence which is not known in the natural world through consensus design, and the like, and having a frame of the repeat module, and as a non-limited example thereof, a variable lymphocyte receptor (VLR), a toll-like receptor (TLR), a TV3 protein, an U2A or ribonuclease inhibitor (RI) may be included. In a preferred exemplary embodiment of the present invention, the LRR family protein may include a number of repeat modules as long as fused water soluble polypeptide is capable of being stably expressed, but the number thereof is not limited thereto, wherein the number thereof is preferably 1 to 9. In addition, the number of the LRR repeat modules may be all numbers including the number known in the natural world as well as the numbers in which the frame of the fused polypeptide is capable of being maintained while artificially adding or removing the module.

In the present invention, the modified repeat module of the VLR protein may include the following repeat module pattern:

LxxLxxLxLxxN.

In the pattern above, L is alanine, glycine, phenylalanine, tyrosine, leucine, isoleucine, valine, or tryptophan; N is asparagine, glutamine, serine, cysteine or threonine and x is any amino acid.

In the present invention, the term "mutation" or "modification" may include all substitution, deletion, or insertion of amino acid residues; preferably, substitution of the existing amino acid residue with the other amino acid residue.

In an exemplary embodiment of the present invention, the polypeptide in which the modified repeat module of the VLR protein and the C-terminal of the VLR protein are fused is characterized by consisting of polypeptide amino acid sequences represented by SEQ ID NOs: 6 to 8. SEQ ID NOs: 6 to 8 correspond to position NOs: 84 to 266 of the amino acid of SEQ ID NOs: 3 to 5.

In still another aspect, the present invention is directed to a polynucleotide which encodes the repebody according to the present invention.

The polynucleotide may be a polynucleotide having homology of 75%, preferably 85%, more preferably 90%, further preferably 95% or more, and having a polypeptide activity specifically bound to IgG, but the present invention is not limited thereto. In view of an object of the present invention, it is obvious that the polypeptide (repebody) specifically bound to IgG may include polypeptide wherein one or more amino acid residues in the repebody represented by SEQ ID NOs: 3 to 5 is substituted, deleted, or added, as the scope of the present invention.

In still another aspect, the present invention is directed to a vector which contains the polynucleotide (repebody).

In the present invention, the term "vector" may be a DNA product containing base sequence of polynucleotide encoding a target protein operably connected to an appropriate regulation sequence so as to express the target protein in a suitable host cell. The regulation sequence may include a promoter capable of initiating transcription, an any operator sequence for regulating transcription, a sequence encoding an appropriate mRNA ribosome binding site, and a sequence regulating termination of transcription and decoding and may be variously produced depending on a purpose. The promoter of the vector may be constitutive or inducible. The vector may be transfected into a suitable host and then may be replicated or may perform functions regardless of the host genome, and may be integrated into a genome itself.

The vector used in the present invention is not particularly limited as long as it is replicated in host cells, and may be any vector known in the art. Examples of the generally used vector may include plasmid, phagemid, cosmid, virus, and bacteriophage in a natural state or a recombinant state. For example, as the phage vector or the cosmid vector, pWE15, M13, λMBL3, λMBL4, λIXII, λASHII, λt10, λt11, Charon4A, and Charon21A may be used, and as the plastmid vector, pBR-based, pUC-based, pBluescriptII-based, pGEM-based, pTZ-based, pCL-based and pET-based, may be used. The vector usable in the present invention is not particularly limited but may be any known expression vector. Preferably, pACYC177, pACYC184, pCL, pECCG117, pUC19, pBR322, pMW118, pCC1BAC vectors, and the like, may be used. Most preferably, pACYC177, pCL and pCC1BAC vectors may be used.

In still another aspect, the present invention is directed to a recombinant microorganism in which the polynucleotide (repebody) or the vector which contains the polynucleotide (repebody) is introduced.

In the present invention, the term "recombinant microorganism" means a transfected cell in which a vector having polynucleotide encoding one or more target proteins is introduced into a host cell, or polynucleotide encoding one or more target proteins is introduced into a microorganism, such that the polynucleotide is integrated into the chromosome to express the target protein, and may include all cells of eukaryotic cells, prokaryotic cells, and the like. Examples thereof may include bacteria cells such as $E.\ coli,\ streptomyces,\ salmonella\ typhimurium$, and the like; yeast cells; fungus cells such as pichiapastoris, and the like; insect cells such as $drosophila,\ spodoptera$ Sf9 cell, and the like; animal cells such as CHO, COS, NSO, 293, bow melanoma cell, and the like, but the present invention is not particularly limited thereto.

In the present invention, the term "transfection" means that a vector containing polynucleotide encoding a target protein is introduced into a host cell or a polynucleotide encoding a target protein is integratedly completed into chromosome of the host cell, such that protein encoded by the polynucleotide is capable of being expressed in the host cell. The polynucleotide may be any one regardless of the position as long as the polynucleotide is capable of being expressed in the host cell, regardless of the matter that the polynucleotide is inserted and positioned into chromosome of the host cell or positioned on an outer portion of the chromosome. In addition, the polynucleotide includes DNA and RNA encoding the target protein. The polynucleotide may be inserted with any type as long as the polynucleotide is capable of being introduced into the host cell to be expressed. For example, the polynucleotide may be introduced into the host cell as an expression cassette which is a gene structure, including all factors required for self expression. The expression cassette may include a promoter, transcription termination signal, ribosome binding site and translation termination signal which may be operably connected to the polynucleotide. The expression cassette may be an expression vector performing self-replication. In addition, the polynucleotide may be introduced into the host cell as itself to be operably connected to the sequence required for expression in the host cell.

In still another aspect, the present invention is directed to a method for producing a repebody against IgG, wherein the method comprises: (i) expressing the repebody by culturing a recombinant microorganism; and (ii) recovering the expressed repebody.

In the method, the culturing of the recombinant microorganism may be preferably performed by a batch culture method, a continuous culture method, a fed-batch culture, and the like, known in the art, but the present invention not particularly limited thereto, wherein under the culture condition, pH may be appropriately adjusted (pH 5 to 9, preferably pH 6 to 8, most preferably pH 6.8) by using a basic compound (for example: sodium hydroxide, potassium hydroxide or ammonia) or an acidic compound (for example, phosphoric acid or sulfuric acid), and an aerobic condition may be maintained by introducing oxygen, or an oxygen-containing gas mixture into the culture, and the culture may be performed at 20 to 45° C., preferably, 25 to 40° C. for about 10 to 160 hours. The repebody produced by the culture may be secreted in the medium or remained in the cell.

In addition, in the culture medium used, as carbon source, sugar and carbohydrate (for example, glucose, sucrose, lactose, fructose, maltose, molasse, starch and cellulose), oil and fat (for example, soybean oil, sunflower seed oil, peanut oil and coconut oil), fatty acid (for example, palmitic acid, stearic acid and linoleic acid), alcohol (for example, glycerol and ethanol) and organic acid (for example, acetic acid), and the like, may be used individually or by mixing; as nitrogen source, nitrogen-containing organic compound (for example, peptone, yeast extract, gravy, malt extract, corn steep liquor, soybean meal powder and urea), or inorganic compound (for example, ammonium sulfate, ammonium chloride, ammonium phosphate, ammonium carbonate and ammonium nitrate) and the like, may be used individually or by mixing; as phosphate source, potassium dihydrogen phosphate, dipotassium hydrogen phosphate, sodium-containing salt corresponding thereof, and the like, may be used individually or by mixing; or essential growth-promoting materials such as other metal salts (for example, magnesium sulfate or iron sulfate), amino acids and vitamins may be included.

In the recovering of the repebody produced in the culturing of the present invention, the desired repebody may be recovered from a culture fluid by appropriate culture methods such as a batch culture method, a continuous culture method, a fed-batch culture, and the like, known in the art.

In still another aspect, the present invention is directed to a method for purifying an immunoglobulin G antibody, wherein the method comprises: (i) treating a column onto which the repebody according to the present invention is adsorbed with a composition comprising an antibody; and (ii) eluting the antibody attached to the column of the step (i) above.

Here, a bead onto which the repebody is attached may be packed into a column instead of directly adsorbing the repebody onto the column in the step (i) above. The repebody according to the present invention is preferably a repebody consisting of any one amino acid sequence of SEQ ID NOs: 3 to 5.

In still another aspect, the present invention is directed to a method for immobilizing an immunoglobulin G, wherein the method comprises: (i) surface-treating a solid substrate by attaching the repebody according to the present invention onto the solid substrate; and (ii) binding an immunoglobulin G to the surface-treated solid substrate.

The repebody according to the present invention is preferably a repebody consisting of any one amino acid sequence of SEQ ID NOs: 3 to 5.

In the method, the solid substrate may be selected from a group consisting of a CM-5 Au sensor chip, a magnetic micro bead, a glass plate, a gold nanoparticle, a biodegradable organic polymer nanoparticle such as PLGA, and various kinds of micro well plates. IgG used in the present invention is preferably human IgG, but is not limited thereto. By the surface-treating of the step (i) above, the solid substrate may be bound to protein so that orientation is controlled and may have an increased uniformity on a surface thereof. The method of immobilizing IgG using the repebody of the present invention may be physically and chemically stable and may have a significantly wide use thereof as compared to the existing method of using antibody-binding protein (protein A, G, A/G or L) and may be economical as compared to the existing method of using a low molecular compound or protein A.

In still another aspect, the present invention is directed to an immunosensor in which an immunoglobulin G is immobilized onto a solid substrate surface-treated with the repebody according to the present invention, using the repebody as a mediator.

The immunosensor may be obtained by surface-treating the solid substrate with the repebody according to the present specifically bound to Fc site of IgG and immobilizing IgG to be detected. The detection by an antigen-antibody reaction using the immunosensor may vary depending on the kind of the solid substrate. For example, in a case where the solid substrate is a magnetic micro beads, the magnetic micro beads itself may be boiled in buffer and then measured by a PAGE method. In addition, in a case where the solid substrate is a glass plate, the repebody may be treated with fluorescent-labeled IgG to measure fluorescence.

Hereinafter, the present invention will be described in more detail with reference to the following Examples. However, the following Examples are provided by way of example so as to easily explain description and scope of the technical spirit of the present invention. Accordingly, the scope of the present invention is not restricted thereby or changed therefrom. In addition, various modifications and changes may be made by those skilled in the art to which the present invention pertains from this description.

EXAMPLES

Example 1

Design of Phagemid for Selection of Random Repebody Library

A protein frame named repebody was used as a component of the present invention. The frame is a water soluble polypeptide in which an LRR portion containing an N-terminal of an internalin B protein and a C-terminal of VLR protein is fused, and has an amino acid sequence the same as SEQ ID NO: 14.

Example 1-1

Expression of Repebody Using Signal Sequence in Periplasm

In order to confirm whether or not the repebody is applicable to a phage display, it is required to confirm periplasmic expression of *E. coli* to be used as a host, and whether or not protein is well expressed onto a surface particle of a phage. To this end, two recombinant vectors were produced by inserting MalE and DsbA signal sequences which are signal polypeptides differentiated from each other right into the back side of an initiation codon, using pMAL-c2x (NEB, USA) vector. Then, DNA in which the repebody and a histidine-tag are fused was inserted between the signal sequence and termination codon to complete a final vector. Two completed vector was introduced into *E. coli* XL1-blue strain to produce a transformant, the transformant was cultured until absorbance ($OD_{600}$) reached 0.5 and then 0.1 mM IPTG (Isopropyl β-D-1-thiogalactopyranoside) was treated to induce expression of the protein, followed by culturing at 30° C. for 16 hours again. After the culturing was completed, the strain was obtained by centrifugation and treated by ultrasonic wave to obtain a water soluble protein fraction.

Figure 2:
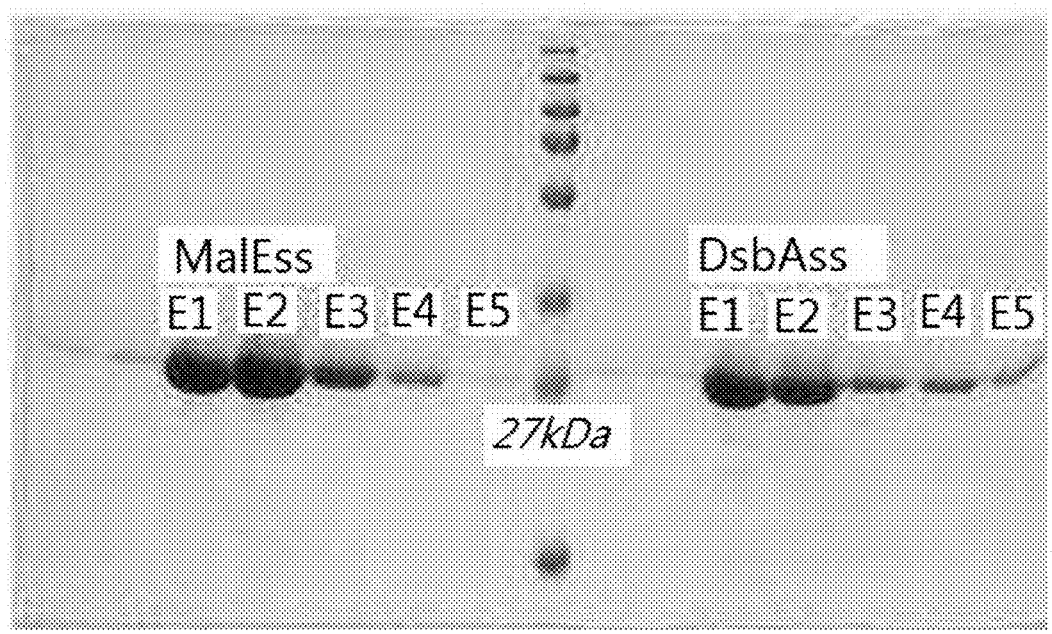
FIG. 2 shows an examination result showing that repebody is expressed in periplasm through two different signal sequences, confirmed by SDS-PAGE; Here, E is the number of eluate, and 27 KDa in the middle means a position of the used standard marker.

The obtained water soluble protein fraction was applied to a Ni-NTA (Nickel-nitrilotriacetic acid) resin to be purified, and an expression amount of the produced repebody in periplasm was confirmed by SDS-PAGE analysis (FIG. 2). FIG. 2 shows an examination result showing repebody expressed in periplasm through two different signal sequences, confirmed by SDS-PAGE, wherein E means the number of eluate, and 27 KDa in the middle means a position of the used standard marker. As shown in FIG. 2, it was confirmed that the MalE signal sequence had a periplasmic expression amount slightly higher than that of the DsbA signal sequence.

Example 1-2

Construct of Phagemid for Repebody Expression on Surface of Phage

Figure 3:
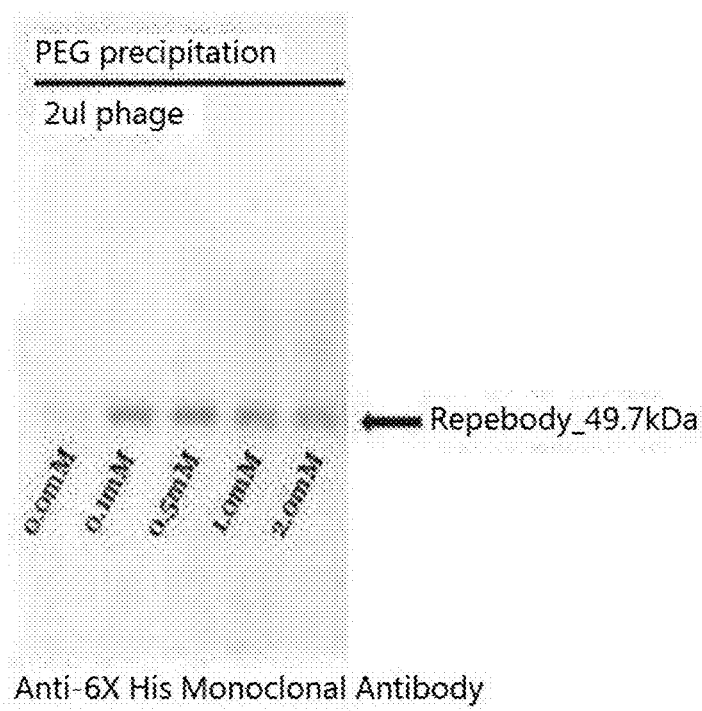
FIG. 3 shows an analysis result of Western Blot for confirming that repebody is expressed on a surface of phage, using phagemid pBEL118M of the present invention, wherein the mM unit means a concentration of IPTG used in induction of the promoter.

A phagemid was designed based on the MalE signal sequence finally determined in Example 1-1 above. With pTV118N (Takara, Japan) as a basic frame, the MalE signal sequence was inserted right into the back side of the initiation codon and DNA in which the repebody and a histidine-tag are fused was added to thereby construct a phagemid. In addition, gp3 which is capable of labeling a relatively large protein among several phage surface proteins was used, C-terminal was positioned at the back of an amber codon, and two continuous terminal codons were finally inserted thereto, thereby completing the phagemid named pBEL118M. The phagemid was introduced into XL1-Blue to produce a transformant, and the produced transformant was cultured by the same method as Example 1-1 above except for treatment with 0.5 mM IPTG, followed by centrifugation to obtain a culture fluid. The culture fluid was applied to Polyethylene glycol precipitation method to purify the phage. The phage was analyzed by Western Blot, and as a result thereof, it was confirmed that the repebody was expressed on a surface of the phage (FIG. 3). FIG. 3 is a view showing an analysis result of Western Blot for confirming that repebody is expressed on a surface of phage, using phagemid pBEL118M of the present invention, wherein the mM unit means a concentration of IPTG used in induction of the promoter.

Example 2

Construct of Repebody Library Based on Protein Structure

The repebody consists of continuously connected repeat units having conserved leucine sequence, similar to LRR proteins present in the natural world and has a modularity maintaining the entire protein structure and structural characteristic of a concave region and a convex region differentiated by curvature of the entire structure (FIG. 4). FIG. 4 is a schematic diagram showing an entire protein structure of repebody, divided into a concave region recognizing biomolecule and a convex region which is important in maintaining the structure. A hypervariable region like a complementarity determining region (CDR) was positioned in the concave region to mediate a protein-protein interaction. In addition, the convex region is important to maintain the entire structure of LRR based on the well conserved sequence. The protein structure of the repebody was analyzed and a random library was designed by the following scheme.

Figure 5:
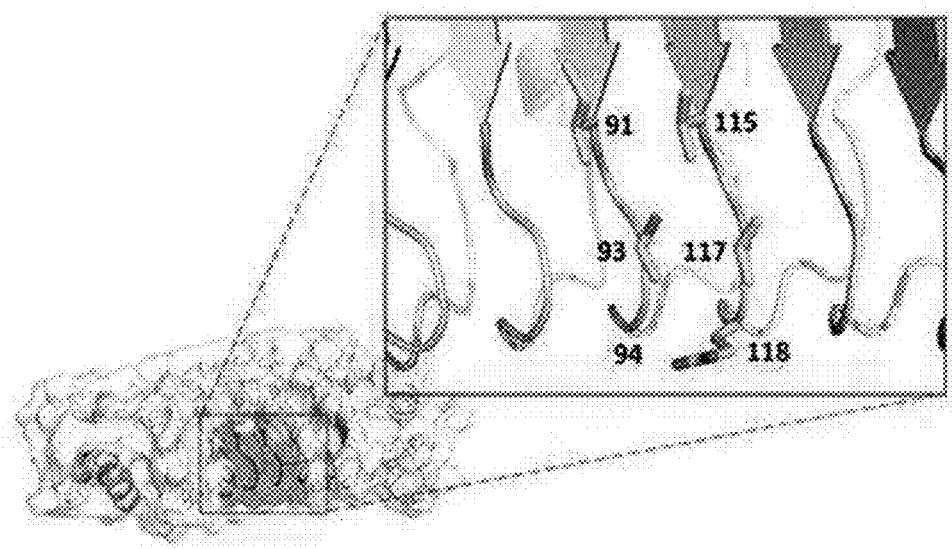
FIG. 5 is a schematic diagram showing an entire structure in which amino acid residues for constructing a random library are indicated.

In detail, six amino acid residues Nos. 91, 93, 94, 115, 117 and 118 positioned at the concave region of two continuous mutation modules (LRRV module 1 and 2) positioned at an amine group terminus were selected in order to deviate from steric hinderance by C-term loop of a non-designed carboxylic acid terminus (FIG. 5). FIG. 5 is a schematic diagram showing an entire structure including amino acid residues for constructing a random library.

Then, the selected amino acid was substituted with NNK degenerate codon and configured so that base sequences of the other convex region include silent mutation, thereby synthesizing a mutagenic primer for constructing a library.

Next, overlap PCR was performed on two modules using the primers to obtain a library DNA (FIG. 1) and the library DNA was inserted into the phagemid pBEL118M to secure a final library phagemid. FIG. 1 is a schematic diagram showing the entire overlap PCR performed based on a module. Each yellow part indicates a variable repeat module and a total of four variable repeat modules are positioned on a polypeptide. A red linear rod indicates a primer used in experiments and a green part of the primer indicates sequence of a concave region containing NNK degenerate codon.

The secured library was introduced into $E.\ coli$ XL1-Blue by electroporation to obtain a transformant, such that a library having a synthetic diversity with a level of $1.8 \times 10^8$ was constructed.

Example 3

Selection of Protein Specifically Bound to IgG Using Phage Display

Example 3-1

Selection of Polypeptide Bound to IgG Through Purification and Panning of Repebody Library Phage The library constructed in Example 2 was cultured by the method of Example 1-1 above and the phage in which the repebody was expressed on a surface thereof was selected by the method of Example 1-2 and purified. In order to select a candidate capable of binding IgG, 10 ug/ml of Fc fragment of IgG was coated on immuno tube at 4° C. for 12 hours or more. The tube was washed with PBS (Phosphate buffered saline), followed by blocking with a PBS solution (TPBS) containing 1% bovine serum albumin (BSA) and 0.05% Tween 20 at 4° C. for 2 hours. After the blocking, $10^{12}$ cfu (Colony forming unit)/ml of the library phage was reacted at room temperature for 2 hours. Then, the reactant was washed with a PBS solution (TPBS) containing 0.05% Tween 20 total five times for 2 minutes and then washed again with PBC twice. Finally, the reactant was treated with 1 ml 0.2M Gly-HCl (pH2.2) at room temperature for 12 minutes to elute the phage in the tube. The reactant after the elution was neutralized with 60 ul of 1.0M Tris-HCl (pH8.8) and 10 ml XL1-Blue ($OD_{600}$=0.5) which is a host $E.\ coli$ was inserted thereinto, followed by plating on a 2xYT plate. A bio-panning process through a series of process as described above was performed total of three times and the Fc fragment coated on the immuno tube was decreased to be 5 ug/ml, followed by bio-panning twice again. A phenomenon that the phage having a specific binding through each panning process is enriched was observed. The result means that the library phage bound to the Fc fragment of IgG is specifically increased.

Example 3-2

Confirmation of Specific Binding of Selected Repebody to IgG and Sequence Analysis Enzyme-linked immunosorbent assay (ELISA) was performed on the phage selected by the method of Example 3-1 above, using a 96-well plate coated with IgG and BSA. As a result, one specific binding candidate showing absorbance ($OD_{450}$) of IgG five times-higher than that of BSA was selected and the sequence thereof was confirmed.

Example 3-3

Analysis of Property of Specific Binding of Selected Repebody to IgG

Figure 6:
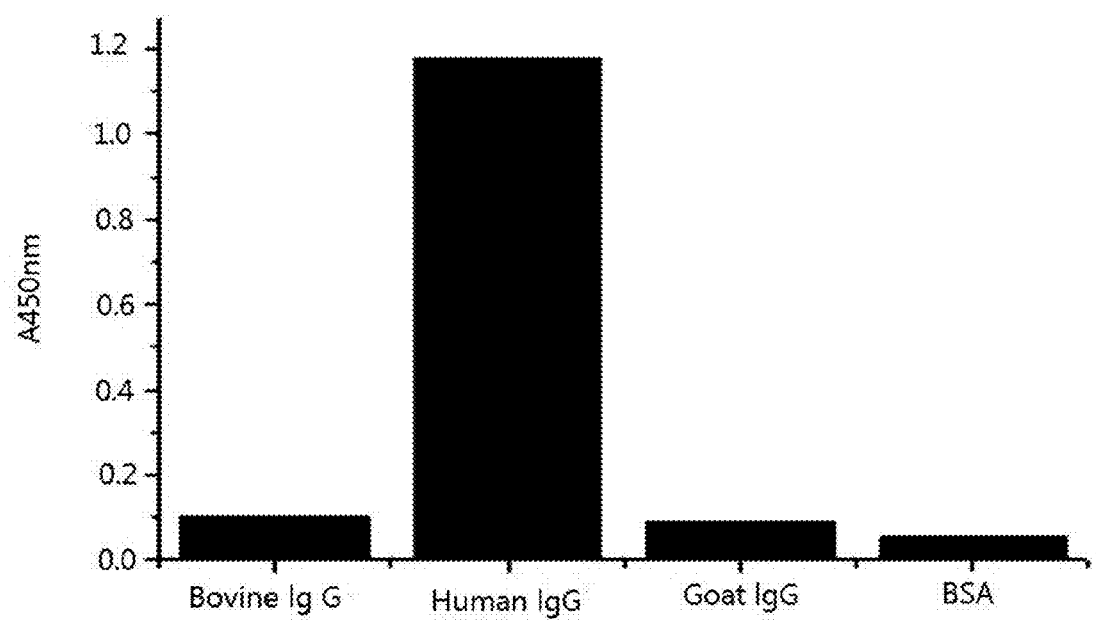
FIG. 6 shows an ELISA result showing that the selected repebody is specifically bound to human IgG.

Based on ELISA result obtained by Example 3-2 above and with the previously obtained Repebody E10 as a target, ELISA was additionally performed using a plate coated with various kinds of IgG and BSA, such that it could be appreciated that the Repebody E10 had a target specificity only on human IgG (FIG. 6).

Figure 7:
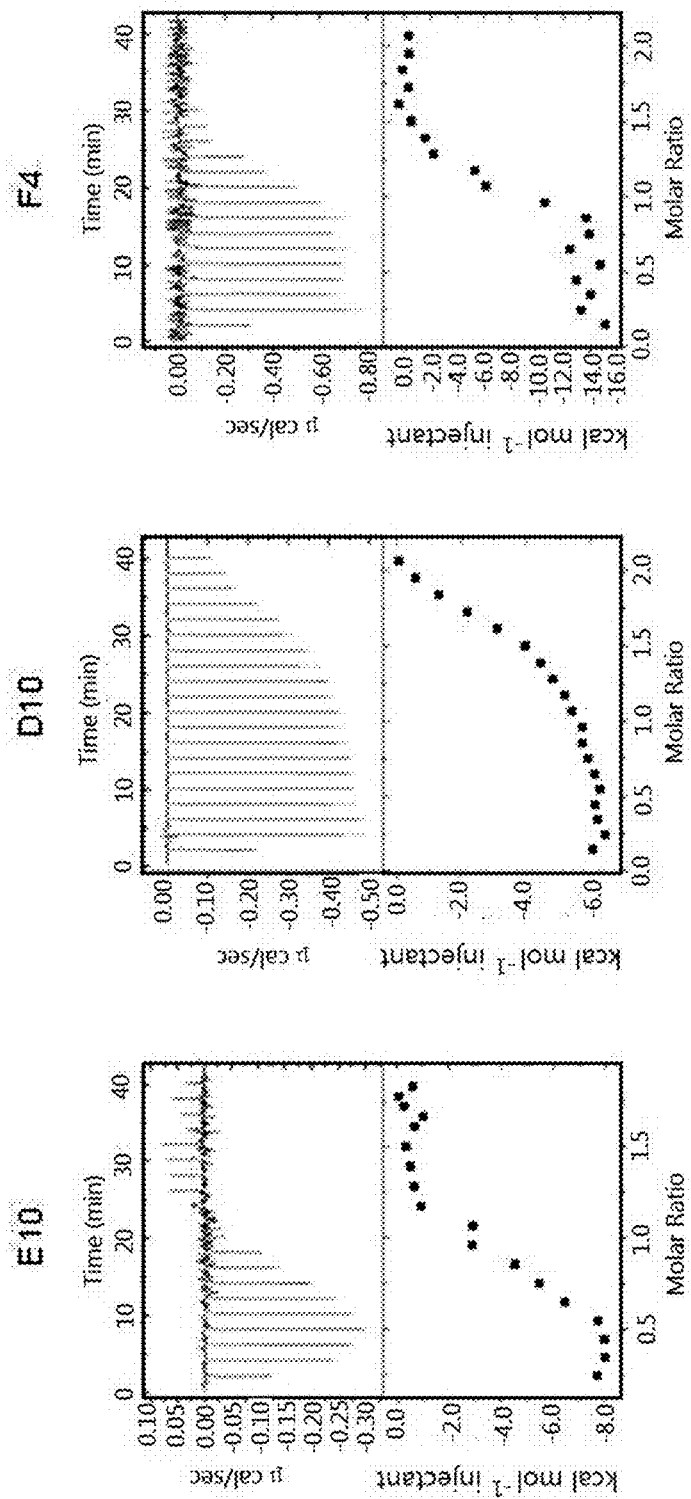
FIG. 7 shows a result obtained by measuring binding capacity between the selected repebody and IgG, by ITC.

Meanwhile, a dissociation constant of the Repebody E10 to IgG was measured. With 0.2 mM (6 mg/ml) of the repebody dissolved into PBS and 0.02 mM (3 mg/ml) of IgG dissolved into PBS, a dissociation constant of the Repebody E10 to IgG was measured at room temperature by Isothermal titration calorimetry (ITC) (FIG. 7). A dissociation constant ($K_D$) of the Repebody E10 to IgG was confirmed as 621 nM.

Example 4-1

Method for Increasing Module-Based Affinity for Increase in Binding Capacity of Repebody It was confirmed from the result of Example 3-3 above that the Repebody E10 is capable of being selectively bound to IgG; however, in order to be used for purification of IgG, and the like, since more various binding capacities need to be secured, mutants having improved binding capacity to IgG was tried to be developed using the modularity of the repebody.

Figure 8:
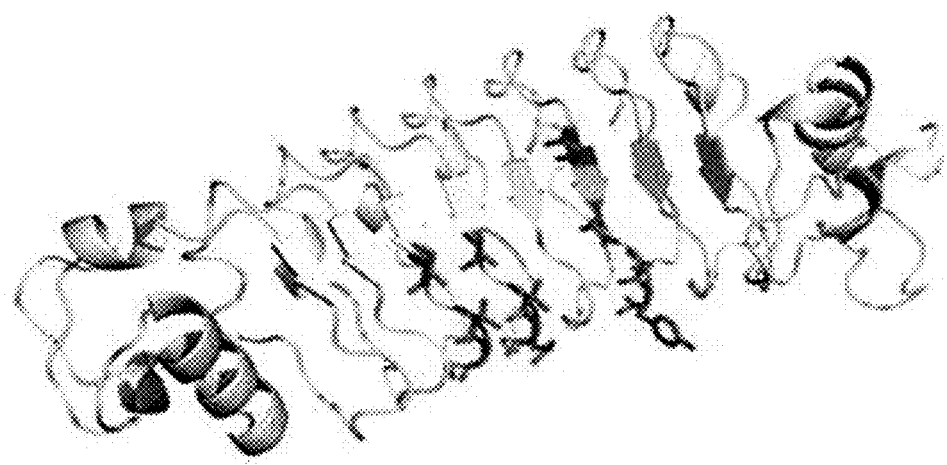
FIG. 8 is a picture showing each position of four residues forming an additional library with Repebody E10 selected in a primary panning process as a basic frame, wherein six residues shown in the two front modules indicate residues substituted at the time of producing a first library and four residues in the rear side indicate residues substituted for producing an additional library.

In detail, the module LRRV module 4 adjacent to the library region constructed by Example 2 above was selected and four residues of the concave region was mutated by the same scheme as Example 2 above (FIG. 8). FIG. 8 is a picture showing each position of the mutated residues of the Repebody E10 as a basic frame at the time of constructing the repebody selectively bound to IgG. Firstly, six residues shown in the two front modules indicate substitution of six amino acid residues positioned on the concave region described in Example 2, and four residues in the back side indicate positions of four residues of the mutated module 4 for constructing a second library. After total five panning processes, two candidates having increased binding capacity (Repebody D10 (SEQ ID NO: 4), Repebody F4 (SEQ ID NO: 5)) were secured and a dissociation constant was measured by ITC, thereby confirming that the binding capacity is increased to a level of 183 to 356 nM (FIG. 7). Four residues of the mutated module 4 is positioned at Nos. 161, 163, 165 and 166 in polypeptide amino acid sequence of the Repebody E10 represented by SEQ ID NO: 3, and it was confirmed that in the repebody D10, the amino acid EDSY at the corresponding position of SEQ ID NO: 3 is substituted with FEEM, and in the repebody F4, the amino acid EDSY at the corresponding position of SEQ ID NO: 3 is substituted with GECG.

Example 4-2

Analysis of Possibility of Replacing Protein a with Selected Repebody

Figure 9:
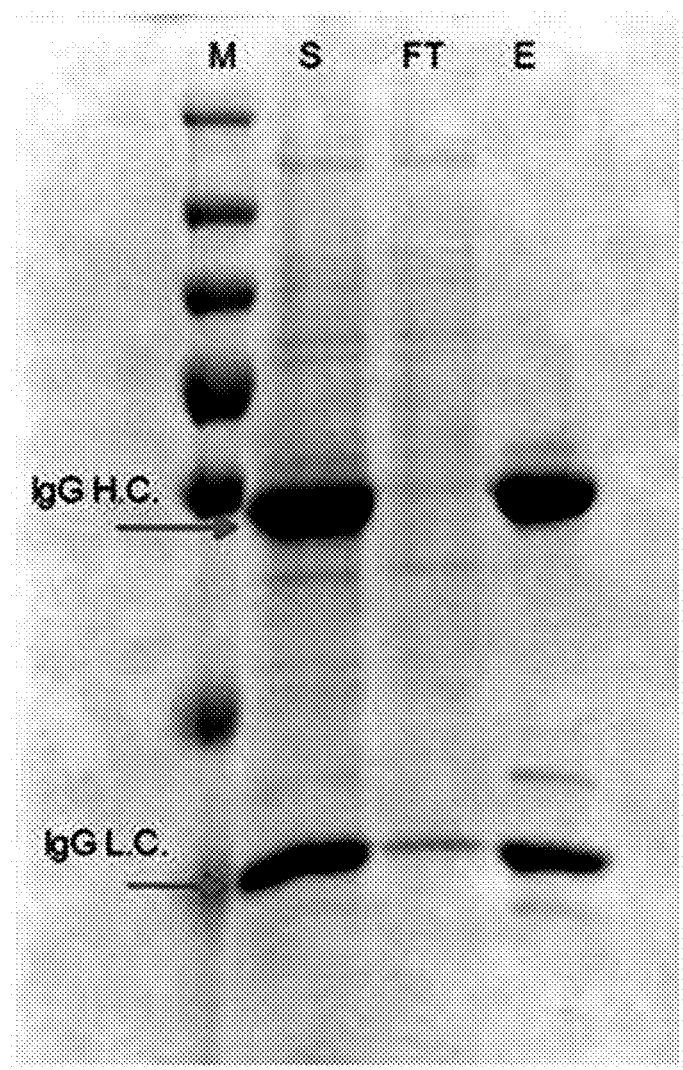
FIG. 9 is a picture confirming a eluted solution under a weak acidic condition (pH 4) after flowing a cell culture fluid containing IgG to polypeptide F4 adsorbed onto a solid surface by SDS-PAGE; S is a flowed cell culture fluid and E is a eluted solution.

In order to analyze possibility of replacing protein A with selected repebodies secured in Examples 3-3 and 4-1, repebody F4 was attached onto a bead surface-treated with N-hydroxysuccinimide (NHS). In order to confirm that the polypeptide attached onto the bead appropriately maintains an activity, the bead onto which the repebody is attached was packed into a column and IgG flowed to the column. Then, the column was washed with a PBS solution and IgG was eluted with pH4 solution and confirmed by SDS PAGE (FIG. 9). As a result thereof, it was confirmed that an antibody was only purified. Therefore, it could be appreciated that the selected repebody of the present invention is substituted by protein A to be capable of being used in purification of an antibody and production of various immunosensors/immune chips, and DDS transporters for drug delivery and targeting, and biological medical products.

The repebody according to the present invention may have excellent binding capacity to IgG, thereby being effectively utilized for purification or immobilization of IgG.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A repebody consisting of the amino acid sequence of SEQ ID NO: 3, wherein the repebody is capable of selectively binding to immunoglobulin G.

2. A repebody consisting of the amino acid sequence of SEQ ID NOs: 4 or 5, wherein the repebody is capable of selectively binding to immunoglobulin G.

3. A polynucleotide which encodes the repebody of claim 1.

4. A vector which contains the polynucleotide of claim 3.

5. A recombinant microorganism, in which the polynucleotide of claim 3, or a vector containing said polynucleotide, is introduced.

6. A method for producing the repebody of claim 1, wherein the method comprises:
   (i) expressing the repebody by culturing the recombinant microorganism of claim 5; and
   (ii) recovering the expressed repebody.

* * * * *

UNITED STATES PATENT AND TRADEMARK OFFICE
CERTIFICATE OF CORRECTION

PATENT NO.        : 9,777,046 B2
APPLICATION NO.   : 14/322864
DATED             : October 3, 2017
INVENTOR(S)       : Hak-Sung Kim et al.

Page 1 of 1

It is certified that error appears in the above-identified patent and that said Letters Patent is hereby corrected as shown below:

In the Specification

Column 2, Line 65: "green part of the printer" should be --green part of the primer--.

Signed and Sealed this
Second Day of January, 2018

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 14

<210> SEQ ID NO 1
<211> LENGTH: 798
<212> TYPE: DNA
<213> ORGANISM: Artificial
<220> FEATURE:
<223> OTHER INFORMATION: Repebody-Library
<220> FEATURE:
<221> NAME/KEY: misc_feature
<222> LOCATION: (271)..(272)
<223> OTHER INFORMATION: n is a, c, g, or t
<220> FEATURE:
<221> NAME/KEY: misc_feature
```

```
<222> LOCATION: (277)..(278)
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t
<220> FEATURE:
<221> NAME/KEY: misc_feature
<222> LOCATION: (343)..(344)
<223> OTHER INFORMATION: n is a, c, g, or t
<220> FEATURE:
<221> NAME/KEY: misc_feature
<222> LOCATION: (349)..(350)
<223> OTHER INFORMATION: n is a, c, g, or t
<220> FEATURE:
<221> NAME/KEY: misc_feature
<222> LOCATION: (352)..(353)
<223> OTHER INFORMATION: n is a, c, g, or t

<400> SEQUENCE: 1
gaaaccatta ccgtgagcac cccgatcaaa cagattttc cggatgacgc gttcgccgaa     60
acgatcaaag caaacctgaa gaaaagagc gttaccgatg ctgtcacgca aaatgaactg    120
aacagtattg accagatcat tgcgaataac tccgatatca aatcagtgca aggcattcag   180
tatctgccga atgttcgtta cctggccctg ggtggcaaca actgcatga catctcggca    240 ctgaaagaac tgaccaatct gacgtatctg nnkctgnnkn nkaaccaact gcagagcctg   300
ccgaacggcg tgtttgataa actgacgaac ctgaaagaac tgnnkctgnn knnkaatcaa   360
ctgcagtctc tgccggatgg tgtgttcgac aaactgacca acctgacgta cctgaatctg   420
gctcacaacc aactgcagag tctgccgaaa ggcgtgtttg acaaactgac caatctgacg   480
gaactggatc tgtcctataa ccaactgcag tcactgccgg aaggtgtttt cgacaaactg   540
acccagctga agatctgcg cctgtaccag aatcagctga atcggtccc ggacggcgtg    600 tttgatcgtc tgaccagcct gcagtatatc tggctgcatg ataaccccgtg ggattgcacc   660 tgtccgggta ttcgctacct gtctgaatgg atcaataaac acagtggcgt tgtccgtaac   720
tccgcgggtt cagttgcccc ggattcggcg aaatgctccg gcagcggtaa accggtgcgt   780
agcattattt gcccgacc                                                  798

<210> SEQ ID NO 2
<211> LENGTH: 4615
<212> TYPE: DNA
<213> ORGANISM: Artificial
<220> FEATURE:
<223> OTHER INFORMATION: pBEL118N
<220> FEATURE:
<221> NAME/KEY: misc_feature
<222> LOCATION: (704)..(705)
<223> OTHER INFORMATION: n is a, c, g, or t
<220> FEATURE:
<221> NAME/KEY: misc_feature
<222> LOCATION: (710)..(711)
<223> OTHER INFORMATION: n is a, c, g, or t
<220> FEATURE:
<221> NAME/KEY: misc_feature
<222> LOCATION: (713)..(714)
<223> OTHER INFORMATION: n is a, c, g, or t
<220> FEATURE:
<221> NAME/KEY: misc_feature
<222> LOCATION: (776)..(777)
<223> OTHER INFORMATION: n is a, c, g, or t
<220> FEATURE:
<221> NAME/KEY: misc_feature
<222> LOCATION: (782)..(783)
<223> OTHER INFORMATION: n is a, c, g, or t
<220> FEATURE:
<221> NAME/KEY: misc_feature
<222> LOCATION: (785)..(786)
```

<223> OTHER INFORMATION: n is a, c, g, or t

<400> SEQUENCE: 2

```
acatgttctt tcctgcgtta tcccctgatt ctgtggataa ccgtattacc gcctttgagt        60
gagctgatac cgctcgccgc agccgaacga ccgagcgcag cgagtcagtg agcgaggaag       120
cggaagagcg cccaatacgc aaaccgcctc tccccgcgcg ttggccgatt cattaatgca       180
gctggcacga caggtttccc gactggaaag cgggcagtga gcgcaacgca attaatgtga       240
gttagctcac tcattaggca ccccaggctt tacactttat gcttccggct cgtatgttgt       300
gtggaattgt gagcggataa caatttcaca caggaaacag accatggcca tgaaaataaa       360
acaggtgca cgcatcctcg cattatccgc attaacgacg atgatgtttt ccgcctcggc       420
tctcgccgaa ttcgaaacca ttaccgtgag cacccccgatc aaacagattt ttccggatga     480
cgcgttcgcc gaaacgatca agcaaaacct gaagaaaaag agcgttaccg atgctgtcac       540
gcaaaatgaa ctgaacagta ttgaccagat cattgcgaat aactccgata tcaaatcagt       600
gcaaggcatt cagtatctgc gaatgttcg ttacctggcc ctgggtggca caaactgca        660
tgacatctcg gcactgaaag aactgaccaa tctgacgtat ctgnnkctgn nknnkaacca       720
actgcagagc ctgccgaacg cgtgtttga taaactgacg aacctgaaag aactgnnkct       780
gnnknnkaat caactgcagt ctctgccgga tggtgtgttc gacaaactga ccaacctgac       840
gtacctgaat ctggctcaca accaactgca gagtctgccg aaaggcgtgt ttgacaaact       900
gaccaatctg acggaactgg atctgtccta taccaactg cagtcactgc cggaaggtgt        960
tttcgacaaa ctgacccagc tgaaagatct gcgcctgtac cagaatcagc tgaaatcggt      1020
cccggacggc gtgtttgatc gtctgaccag cctgcagtat atctggctgc atgataaccc      1080
gtgggattgc acctgtccgg gtattcgcta cctgtctgaa tggatcaata acacagtgg       1140
cgttgtccgt aactccgcgg gttcagttgc cccggattcg gcgaaatgct ccggcagcgg      1200
taaaccggtg cgtagcatta tttgcccgac ctcgagcacc accaccacca ccactagggc      1260
ggcggctctg gtggtggttc tggtggcggc tctgagggtg gtggctctga gggtggcggt      1320
tctgagggtg gcggctctga gggaggcggt tccggtggtg gctctggttc cggtgatttt     1380
gattatgaaa agatggcaaa cgctaataag ggggctatga ccgaaaatgc cgatgaaaac      1440
gcgctacagt ctgacgctaa aggcaaactt gattctgtcg ctactgatta cggtgctgct      1500
atcgatggtt tcattggtga cgtttccggc cttgctaatg gtaatggtgc tactggtgat      1560
tttgctggct ctaattccca aatggctcaa gtcggtgacg tgataattc acctttaatg       1620
aataatttcc gtcaatattt accttcctc cctcaatcgg ttgaatgtcg ccctttgtc       1680
tttggcgctg gtaaaccata tgaattttct attgattgtg acaaaataaa cttattccgt      1740
ggtgtctttg cgtttctttt atatgttgcc acctttatgt atgtattttc tacgtttgct      1800
aacatactgc gtaataagga gtcttagtaa ggatcctcta gagtcgacct gcaggcatgc      1860
aagcttggca ctggccgtcg ttttacaacg tcgtgactgg gaaaaccctg gcgttaccca      1920
acttaatcgc cttgcagcac atccccctttt cgccagctgg cgtaatagcg aagaggcccg     1980
caccgatcgc ccttcccaac agttgcgcag cctgaatggc gaatggcgtc taagaaacca     2040
ttattatcat gacattaacc tataaaaata ggcgtatcac gaggcccttt cgtctcgcgc      2100
gtttcggtga tgacggtgaa aacctctgac acatgcagct cccggagacg gtcacagctt     2160
gtctgtaagc ggatgccggg agcagacaag cccgtcaggg cgcgtcagcg ggtgttggcg      2220
ggtgtcgggg ctggcttaac tatgcggcat cagagcagat tgtactgaga gtgcaccata     2280
```

```
aaattgtaaa cgttaatatt ttgttaaaat tcgcgttaaa ttttttgttaa atcagctcat    2340 tttttaacca ataggccgaa atcggcaaaa tcccttataa atcaaaagaa tagcccgaga    2400
tagggttgag tgttgttcca gtttggaaca agagtccact attaaagaac gtggactcca    2460
acgtcaaagg gcgaaaaacc gtctatcagg gcgatggccc actacgtgaa ccatcaccca    2520
aatcaagttt tttggggtcg aggtgccgta agcactaaa tcggaaccct aaagggagcc    2580
cccgatttag agcttgacgg ggaaagccgg cgaacgtggc gagaaaggaa gggaagaaag    2640
cgaaaggagc gggcgctagg gcgctggcaa gtgtagcggt cacgctgcgc gtaaccacca    2700
cacccgccgc gcttaatgcg ccgctacagg gcgcgtacta tggttgcttt gacgtatgcg    2760
gtgtgaaata ccgcacagat gcgtaaggag aaaataccgc atcaggcgtc aggtggcact    2820
tttcggggaa atgtgcgcgg aacccctatt tgtttatttt tctaaataca ttcaaatatg    2880
tatccgctca tgagacaata accctgataa atgcttcaat aatattgaaa aagaagagt    2940 atgagtattc aacatttccg tgtcgccctt attcccttt ttgcggcatt ttgccttcct    3000 gttttgctc acccagaaac gctggtgaaa gtaaaagatg ctgaagatca gttgggtgca    3060
cgagtgggtt acatcgaact ggatctcaac agcggtaaga tccttgagag ttttcgcccc    3120
gaagaacgtt ttccaatgat gagcactttt aaagttctgc tatgtggcgc ggtattatcc    3180
cgtattgacg ccgggcaaga gcaactcggt cgccgcatac actattctca gaatgacttg    3240
gttgagtact caccagtcac agaaaagcat cttacggatg gcatgacagt aagagaatta    3300
tgcagtgctg ccataaccat gagtgataac actgcggcca acttacttct gacaacgatc    3360
ggaggaccga aggagctaac cgcttttttg cacaacatgg gggatcatgt aactcgcctt    3420
gatcgttggg aaccggagct gaatgaagcc ataccaaacg acgagcgtga ccacgatg     3480 cctgtagcaa tggcaacaac gttgcgcaaa ctattaactg gcgaactact tactctagct    3540
tcccggcaac aattaataga ctggatggag gcggataaag ttgcaggacc acttctgcgc    3600
tcggcccttc cggctggctg gtttattgct gataaatctg gagccggtga gcgtgggtct    3660
cgcggtatca ttgcagcact ggggccagat ggtaagccct cccgtatcgt agttatctac    3720
acgacgggga gtcaggcaac tatggatgaa cgaaatagac agatcgctga tataggtgcc    3780
tcactgatta agcattggta actgtcagac caagtttact catatatact ttagattgat    3840
ttaaaacttc attttttaatt taaaaggatc taggtgaaga tccttttttga taatctcatg    3900 accaaaatcc cttaacgtga gttttcgttc cactgagcgt cagaccccgt agaaaagatc    3960
aaaggatctt cttgagatcc tttttttctg cgcgtaatct gctgcttgca acaaaaaaaa    4020
ccaccgctac cagcggtggt ttgtttgccg gatcaagagc taccaactct ttttccgaag    4080
gtaactggct tcagcagagc gcagatacca aatactgtcc ttctagtgta gccgtagtta    4140
ggccaccact tcaagaactc tgtagcaccg cctacatacc tcgctctgct aatcctgtta    4200
ccagtggctg ctgccagtgg cgataagtcg tgtcttaccg ggttggactc aagacgatag    4260
ttaccggata aggcgcagcg gtcgggctga acggggggtt cgtgcacaca gcccagcttg    4320
gagcgaacga cctacaccga actgagatac ctacagcgtg agctatgaga aagcgccacg    4380
cttcccgaag ggagaaaggc ggacaggtat ccggtaagcg gcagggtcgg aacaggagag    4440
cgcacgaggg agcttccagg gggaaacgcc tggtatcttt atagtcctgt cgggtttcgc    4500
cacctctgac ttgagcgtcg atttttgtga tgctcgtcag ggggggcggag cctatggaaa    4560 aacgccagca acgcggcctt tttacggttc ctggccttt gctggccttt tgctc        4615
```

<210> SEQ ID NO 3
<211> LENGTH: 266
<212> TYPE: PRT
<213> ORGANISM: Artificial
<220> FEATURE:
<223> OTHER INFORMATION: Repebody-E10

<400> SEQUENCE: 3

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Glu Leu Lys Trp Asn Gln
                85                  90                  95

Leu Gln Ile Leu Pro Asn Gly Val Phe Asp Lys Leu Thr Asn Leu Lys
            100                 105                 110

Glu Leu Val Leu Asn Ser Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 4
<211> LENGTH: 266
<212> TYPE: PRT
<213> ORGANISM: Artificial
<220> FEATURE:
<223> OTHER INFORMATION: Repebody-D10

<400> SEQUENCE: 4

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

```
Asn Asn Ser Asp Ile Lys Ser Val Gln Gly Ile Gln Tyr Leu Pro Asn
            50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Glu Leu Lys Trp Asn Gln
                    85                  90                  95

Leu Gln Ile Leu Pro Asn Gly Val Phe Asp Lys Leu Thr Asn Leu Lys
                    100                 105                 110

Glu Leu Val Leu Asn Ser Asn Gln Leu Gln Ser Leu Pro Asp Gly Val
            115                 120                 125

Phe Asp Lys Leu Thr Asn Leu Thr Tyr Leu Asn Leu Ala His Asn Gln
            130                 135                 140

Leu Gln Ser Leu Pro Lys Gly Val Phe Asp Lys Leu Thr Asn Leu Thr
145                 150                 155                 160

Phe Leu Glu Leu Glu Met Asn Gln Leu Gln Ser Leu Pro Glu Gly Val
                    165                 170                 175

Phe Asp Lys Leu Thr Gln Leu Lys Asp Leu Arg Leu Tyr Gln Asn Gln
                    180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                    245                 250                 255

Lys Pro Val Arg Ser Ile Ile Cys Pro Thr
            260                 265

<210> SEQ ID NO 5
<211> LENGTH: 266
<212> TYPE: PRT
<213> ORGANISM: Artificial
<220> FEATURE:
<223> OTHER INFORMATION: Repebody-F4

<400> SEQUENCE: 5

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
            50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Glu Leu Lys Trp Asn Gln
                    85                  90                  95

Leu Gln Ile Leu Pro Asn Gly Val Phe Asp Lys Leu Thr Asn Leu Lys
                    100                 105                 110

Glu Leu Val Leu Asn Ser Asn Gln Leu Gln Ser Leu Pro Asp Gly Val
            115                 120                 125

Phe Asp Lys Leu Thr Asn Leu Thr Tyr Leu Asn Leu Ala His Asn Gln
            130                 135                 140
```

Leu Gln Ser Leu Pro Asp Gly Val Phe Asp Lys Leu Thr Asn Leu Thr
145                 150                 155                 160

Gly Leu Glu Leu Cys Gly Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 6
<211> LENGTH: 183
<212> TYPE: PRT
<213> ORGANISM: Artificial
<220> FEATURE:
<223> OTHER INFORMATION: fused polypeptide of repeat module of VLR
      protein and C-terminal of VLR protein

<400> SEQUENCE: 6

Leu Thr Asn Leu Thr Tyr Leu Glu Leu Lys Trp Asn Gln Leu Gln Ile
1               5                   10                  15

Leu Pro Asn Gly Val Phe Asp Lys Leu Thr Asn Leu Lys Glu Leu Val
            20                  25                  30

Leu Asn Ser Asn Gln Leu Gln Ser Leu Pro Asp Gly Val Phe Asp Lys
        35                  40                  45

Leu Thr Asn Leu Thr Tyr Leu Asn Leu Ala His Asn Gln Leu Gln Ser
    50                  55                  60

Leu Pro Lys Gly Val Phe Asp Lys Leu Thr Asn Leu Thr Glu Leu Asp
65                  70                  75                  80

Leu Ser Tyr Asn Gln Leu Gln Ser Leu Pro Glu Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
        115                 120                 125

Leu His Asp Asn Pro Trp Asp Cys Thr Cys Pro Gly Ile Arg Tyr Leu
    130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180

<210> SEQ ID NO 7
<211> LENGTH: 183
<212> TYPE: PRT
<213> ORGANISM: Artificial
<220> FEATURE:
<223> OTHER INFORMATION: fused polypeptide of repeat module of VLR protein and C-terminal of VLR protein

<400> SEQUENCE: 7

```
Leu Thr Asn Leu Thr Tyr Leu Glu Leu Lys Trp Asn Gln Leu Gln Ile
1               5                   10                  15

Leu Pro Asn Gly Val Phe Asp Lys Leu Thr Asn Leu Lys Glu Leu Val
                20                  25                  30

Leu Asn Ser Asn Gln Leu Gln Ser Leu Pro Asp Gly Val Phe Asp Lys
            35                  40                  45

Leu Thr Asn Leu Thr Tyr Leu Asn Leu Ala His Asn Gln Leu Gln Ser
        50                  55                  60

Leu Pro Lys Gly Val Phe Asp Lys Leu Thr Asn Leu Thr Phe Leu Glu
65                  70                  75                  80

Leu Glu Met Asn Gln Leu Gln Ser Leu Pro Glu Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
        130                 135                 140

Ser Glu Trp Ile Asn Lys His Ser Gly Val Val Arg Asn Ser Ala Gly
145                 150                 155                 160

Ser Val Ala Pro Asp Ser Ala Lys Cys Ser Gly Ser Gly Lys Pro Val
                165                 170                 175

Arg Ser Ile Ile Cys Pro Thr
            180
```

<210> SEQ ID NO 8
<211> LENGTH: 183
<212> TYPE: PRT
<213> ORGANISM: Artificial
<220> FEATURE:
<223> OTHER INFORMATION: fused polypeptide of repeat module of VLR
      protein and C-terminal of VLR protein

<400> SEQUENCE: 8

```
Leu Thr Asn Leu Thr Tyr Leu Glu Leu Lys Trp Asn Gln Leu Gln Ile
1               5                   10                  15

Leu Pro Asn Gly Val Phe Asp Lys Leu Thr Asn Leu Lys Glu Leu Val
                20                  25                  30

Leu Asn Ser Asn Gln Leu Gln Ser Leu Pro Asp Gly Val Phe Asp Lys
            35                  40                  45

Leu Thr Asn Leu Thr Tyr Leu Asn Leu Ala His Asn Gln Leu Gln Ser
        50                  55                  60

Leu Pro Asp Gly Val Phe Asp Lys Leu Thr Asn Leu Thr Gly Leu Glu
65                  70                  75                  80

Leu Cys Gly Asn Gln Leu Gln Ser Leu Pro Glu Gly Val Phe Asp Lys
                85                  90                  95

Leu Thr Gln Leu Lys Asp Leu Arg Leu Tyr Gln Asn Gln Leu Lys Ser
            100                 105                 110

Val Pro Asp Gly Val Phe Asp Arg Leu Thr Ser Leu Gln Tyr Ile Trp
            115                 120                 125

Leu His Asp Asn Pro Trp Asp Cys Thr Cys Pro Gly Ile Arg Tyr Leu
        130                 135                 140

Ser Glu Trp Ile Asn Lys His Ser Gly Val Val Arg Asn Ser Ala Gly
```

```
                145                 150                 155                 160
Ser Val Ala Pro Asp Ser Ala Lys Cys Ser Gly Ser Gly Lys Pro Val
                165                 170                 175
Arg Ser Ile Ile Cys Pro Thr
            180

<210> SEQ ID NO 9
<211> LENGTH: 39
<212> TYPE: PRT
<213> ORGANISM: Artificial
<220> FEATURE:
<223> OTHER INFORMATION: partial N-terminal fragment of Internalin
      protein

<400> SEQUENCE: 9

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu
            35

<210> SEQ ID NO 10
<211> LENGTH: 83
<212> TYPE: PRT
<213> ORGANISM: Artificial
<220> FEATURE:
<223> OTHER INFORMATION: N-terminal of Internalin B
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid

<400> SEQUENCE: 10

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45
```

```
Asn Asn Ser Asp Ile Lys Ser Val Gln Gly Ile Gln Tyr Leu Pro Xaa
            50                  55                  60

Leu Xaa Xaa Leu Xaa Leu Xaa Xaa Asn Xaa Ile Xaa Asp Ile Xaa Xaa
 65              70              75                  80

Leu Xaa Xaa

<210> SEQ ID NO 11
<211> LENGTH: 83
<212> TYPE: PRT
<213> ORGANISM: Artificial
<220> FEATURE:
<223> OTHER INFORMATION: N-terminal of Internalin protein

<400> SEQUENCE: 11

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
            50                  55                  60

Val Arg Tyr Leu Ala Leu Gly Gly Asn Lys Leu His Asp Ile Ser Ala
 65              70              75                  80

Leu Lys Glu

<210> SEQ ID NO 12
<211> LENGTH: 83
<212> TYPE: PRT
<213> ORGANISM: Artificial
<220> FEATURE:
<223> OTHER INFORMATION: N-terminal of Internalin protein

<400> SEQUENCE: 12

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
            50                  55                  60

Val Arg Tyr Leu Ala Leu Gly Gly Asn Lys Leu His Asp Ile Ser Ala
 65              70              75                  80

Leu Lys Glu

<210> SEQ ID NO 13
<211> LENGTH: 83
<212> TYPE: PRT
<213> ORGANISM: Artificial
<220> FEATURE:
<223> OTHER INFORMATION: N-terminal of Internalin protein

<400> SEQUENCE: 13

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
```

```
                35                  40                  45
Asn Asn Ser Asp Ile Lys Ser Val Gln Gly Ile Gln Tyr Leu Pro Asn
         50                  55                  60

Val Arg Tyr Leu Ala Leu Gly Gly Asn Lys Leu His Asp Ile Ser Ala
 65                  70                  75                  80

Leu Lys Glu

<210> SEQ ID NO 14
<211> LENGTH: 266
<212> TYPE: PRT
<213> ORGANISM: Artificial
<220> FEATURE:
<223> OTHER INFORMATION: Repebody-MD2

<400> SEQUENCE: 14

Glu Thr Ile Thr Val Ser Thr Pro Ile Lys Gln Ile Phe Pro Asp Asp
  1               5                  10                  15

Ala Phe Ala Glu Thr Ile Lys Ala Asn Leu Lys Lys Ser Val Thr
                 20                  25                  30

Asp Ala Val Thr Gln Asn Glu Leu Asn Ser Ile Asp Gln Ile Ile Ala
             35                  40                  45

Asn Asn Ser Asp Ile Lys Ser Val Gln Gly Ile Gln Tyr Leu Pro Asn
         50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Ile Leu Thr Gly Asn Gln
                 85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
            115                 120                 125

Phe Asp Lys Leu Thr Asn Leu Thr Tyr Leu Asn Leu Ala His Asn Gln
            130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265
```